United States Patent [19]

Usala

[11] Patent Number: 5,776,324
[45] Date of Patent: Jul. 7, 1998

[54] ELECTROCHEMICAL BIOSENSORS

[75] Inventor: Anton-Lewis Usala, Winterville, N.C.

[73] Assignee: Encelle, Inc., Cleveland, Ohio

[21] Appl. No.: 602,909

[22] Filed: May 17, 1996

[51] Int. Cl.$^6$ .......................... G01N 27/26; G01N 1/10; B32B 5/18; A61L 31/00
[52] U.S. Cl. .................. 204/403; 435/817; 428/423.4; 422/50; 427/2.3; 210/500.27; 210/506; 210/500.28; 210/500.33
[58] Field of Search .................. 205/777.5; 204/403, 204/402; 210/500.27, 506, 500.28, 500.21, 500.33; 422/48, 56, 57, 60, 68.1, 69, 72, 73; 427/2.3, 211; 428/423.4; 435/817, 287.9, 287.2, 243

[56] References Cited

U.S. PATENT DOCUMENTS

| | | | |
|---|---|---|---|
| 3,764,018 | 10/1973 | Shaw et al. | 210/500 |
| 3,878,109 | 4/1975 | Ikeda et al. | 210/500 M |
| 4,340,458 | 7/1982 | Lerner et al. | 204/195 R |
| 4,935,345 | 6/1990 | Guilbeau et al. | 435/14 |
| 4,950,404 | 8/1990 | Chau | 210/500.27 |
| 5,420,038 | 5/1995 | Wall et al. | 436/8 |
| 5,614,205 | 3/1997 | Usala et al. | 424/424 |

FOREIGN PATENT DOCUMENTS

60018749 A2   1/1985   Japan .

OTHER PUBLICATIONS

CAPLUS abstract of "Biocompatibility of glow–discharge–polymerized films and vacuum–deposited parylene", HAhn et al., J. Appl. Polym. Sci.: Appl. Polym. Symp. (1984), 38(Plasma Polym. Plasm. Treat.), 55–64, month unknown 1984.

Chemical Abstracts File registry entry for parylene, month unknown 1997.

Bezdadea et al., "Use of Glycidyls in the Modification of Polyurethane Membrane Structures", Polymer International 32 (1993) 407–410, month unknown 1993.

Sasso et al., "Electropolymerized 1,2–diaminobenzene as a means to prevent interference and fouling and to stabilize immobilized enzyme in electrochemical biosensors", Anal. Chem. (1990), 62(11), 1111–17, month unknow 1990.

JAPIO abstract of JP 60018749 A (Murata MFG Co. Ltd.), Jan. 30, 1985/

David A. Gough et al., Development of the Implantable Glucos Sensor, Diabetes, vol. 44, Sep. 1995.

David A. Gough et al., Progress Toward a Potentially Implantable, Enzyme–Based Glucose Sensor, Diabets Care, vol. 5 No. 3, May–Jun. 1982.

Primary Examiner—Bruce F. Bell
Assistant Examiner—Alex Noguerola
Attorney, Agent, or Firm—BellSeltzer IP Property Group

[57] ABSTRACT

An electrochemical biosensor for determining the level of a target chemical in a biological fluid includes an electrochemical system including a enzyme substrate which reacts with the target chemical to yield a system signal related to the concentration in the biological fluid of said target chemical. The biosensor includes a first membrane for immobilizing the enzyme substrate. The first membrane has a porosity permitting passage therethrough of the target chemical to react with the enzyme substrate and a surface exposed to the biological fluid characterized by electron donor site susceptible to facilitating attachment thereon of proteins and fibrin which impair the system signal. A second membrane is bonded to the electron donor sites of the first membrane. The second membrane is formed of a phenyl based polymer having connecting hydrogen atom donors which bond to the hydrogen atom donors bonding to the electron donor sites at least sufficiently to form an outer surface on the first membrane exposed to the biological fluid consisting of phenyl rings without significantly changing the porosity provided by the first membrane.

11 Claims, 1 Drawing Sheet

ELECTROCHEMICAL BIOSENSORS

FIELD OF THE INVENTION

The present invention relates to means for detecting a broad range of chemicals and biological substances that may be found in blood or other physiological fluids including electrochemical biosensors for determining the levels of chemicals in biological fluids, and in particular, an implantable glucose sensor for determining in vivo the concentration of blood glucose levels.

BACKGROUND OF THE INVENTION

Electrochemical biosensors are used, both in vitro and in vivo, to determine the levels of chemicals in biological fluids. For example, blood glucose sensors are used to determine the concentration of glucose in blood sera. Oxygen sensors are used to measure oxygen levels in blood. Other examples are potassium, calcium, pH, $CO_2$, sodium, chloride sensors and the like. Such sensors use an enzyme, immobilized by a membrane sheathing, coupled to an electrochemical system. The target chemical in the biological fluid reacts with the enzyme to generate a current signal related to the target chemical concentration, which signal is processed by the system to provide an output indicative thereof.

While well defined for in vitro testing and used routinely therefor, there has been a long-felt need in the art for implantable or indwelling biosensors that can function, reliably without drift or recalibrating caused by biological overgrowth and attachment, for extended times in recipient patients. Implantable glucose sensors were first proposed in the 1960's (Gough et. al., Diabetes, Vol. 44, pp. 190–198). However, to date no successful biosensor has been developed notwithstanding advances which have yielded successful in vitro versions which function for somewhat extended periods but are prone to biological overgrowth and fouling. Such biosensors are well characterized in the art and generally fall into the categories of hydrogen peroxide-based enzyme electrode sensors, oxygen-based enzyme electrode sensors, mediator-based enzyme electrode sensors, membrane covered catalytic electrodes and others.

The most significant reason for an inability to function reliably long-term in vivo appears to be biological fouling of the electrode membrane resulting in a progressive reduction in sensing area and resultant drift in electrical signal, ultimately leading to complete blockage of the membrane and the loss of meaningful signal. These membranes currently function adequately in most regards. Examples of such membranes include polyurethane, cellulose acetate, perfluorosulfonic acid polymer Nafion®, and other like membrane materials. Such membranes are considered biocompatible in the sense that they do not elicit an inflammatory responses in the host. However, these membrane materials have reactive groups which provide attachment sites for biological overgrowth leading to the membrane fouling discussed above.

It would thus be desirable to provide an electrochemical biosensor based on current and future designs while protecting the membrane from performance degrading biological overgrowth.

SUMMARY OF THE INVENTION

The present invention achieves the above and other significant objectives and provides an improved electrochemical biosensor that limits biological overgrowth and attachment to the membrane and permits extended indwelling determination of target biological chemicals. This is achieved by passivating the biological active sites on the membrane without significantly affecting the functional properties of the membrane, i.e. porosity and diffusion. This is achieved by applying a second membrane over the first membrane, the second membrane being characterized by a phenyl-based polymer having connecting hydrogen donors bonded to the biologically active sites on the first polymer without significantly affecting the properties of the first membrane. Preferably, the polymer is selected from the parylene family including poly-para-xylylene, mono-chloro-poly-para-xylylene, dichloro-poly-para-xylylene and analogs thereof. The parylene membrane is vacuum deposited on the outer surface of the first membrane in an amount sufficient to occupy the biologically active sites to an extent limiting biological attachment but not significantly affecting the electrochemical performance of the biosensor.

For example, polyurethane membranes have shown some promise as a membrane for glucose sensors. However, the outer surfaces of such membranes have bioactive attachment sites, i.e. oxygen and hydrogen, each of which is well recognized for supporting protein and fibrin attachment. The parylene polymers used in the present invention are phenyl-based polymers having connecting —$CH_2$— groups. Other similar polymers have connecting —NH— groups, —SH— groups or other limited hydrogen atom donors. These phenyl-based polymers such as poly-para-xylylene, adhere to the underlying surface by hydrogen bonding between the connecting —$CH_2$— groups and an oxygen, fluorine, chlorine, or other electron donor on the base membrane substrate. Such hydrogen bonding leaves only the phenyl rings exposed to the surrounding milieu, and thus precludes attachment sites from circulating proteins or cells that would otherwise attach thereto thereby, degrading the sensitivity and accuracy of the electrochemical reaction and resultant signal.

As set forth in greater detail below, a biosensor employing an improved membrane in accordance with the present invention, when implanted in-vivo and removed for testing, yielded a membrane without protein or fibrin attachment. Pre-implant readings and post-implant readings showed a high degree of correlation. In contrast, an uncoated control sensor membrane was occluded with fibrin and protein attachment so as to preclude post removal readings.

The use of the phenyl ring polymers herein differs from the approach taken in copending application U.S. Ser. No. 346,340 filed on Nov. 28, 1994 and assigned to the assignee of the present invention, which is now U.S. Pat. No. 5,614,205. Therein a membrane of the parylene family of polymers was used as a semi-permeable membrane to protect cellular moieties from the patient immune system while allowing cell nutrients, chemical signals for the cellular production, and the chemical moiety produced thereby to flow through the membrane. The thickness of the polymer was the prime determinant of membrane porosity and membrane strength and desirable membranes were produced in the 2,000 to 5,000 Angstroms for monolithic membranes. In contrast, the membrane for providing biological passivation in the present invention is an order or orders of magnitudes thinner to produce the desired porosity, generally 1,000 Angstroms or below depending on the base membrane material. Such an ultra thin membrane would normally not have sufficient mechanical strength to withstand the biological forces of implantation. This is achieved in the present invention because the membrane is deposited conformally and preferentially at the attraction sites on the base membrane, rather than by the cross linking network of only the base polymer. In other words, the base membrane functions more or less like a template for the biologically inert membrane until the active sites are occupied. Depending on the overall properties desired, the coating may be applied in a manner in which only a portion of the sites are bonded to provide the desired biological inertness as needed. The membrane may also be applied in excess to the extent that the desired membrane performance characteristics are not adversely affected.

Accordingly, the present invention provides an electrochemical biosensor for determining the level of a target chemical in a biological fluid wherein an electrochemical system includes a substrate which reacts with the target chemical to yield a system signal related to the concentration in the biological fluid of said target chemical. A first membrane on the biosensor immobilizes the substrate and has a porosity permitting passage therethrough of the target chemical to react with the substrate. The first membrane has a surface exposed to the biological fluid said membrane being characterized by electron donor sites susceptible to facilitating attachment thereon of proteins and fibrin, thus impairing the system signal. A second membrane is bonded to the electron donor sites of said first membrane. The second membrane is formed of a phenyl-based polymer having connecting hydrogen atom donors which bond to the electron donor sites at least sufficiently to form an outer surface on the first membrane exposed to the biological fluid without significantly changing the porosity provided by the first membrane.

Further, the present invention provides a biologically inert membrane composite substrate including a first membrane characterized by a predetermined porosity and formed of a material with biologically active surface sites capable of supporting protein and tissue attachment when exposed to biological fluids. A second membrane consisting of a phenyl based polymer having connecting hydrogen donors is bonded to the biologically active surface sites sufficiently to render such sites biologically inert without significantly affecting the predetermined porosity of the first membrane.

Moreover, the present invention provides a method for biologically passivating a membrane having a porosity permitting passage therethrough of a chemical in a biological fluid and a surface with attractive sites for proteins and fibrin, wherein a phenyl-based polymer having connecting hydrogen bond donors is bonded to the attractive sites in an amount sufficient to render the surface biologically inert but insufficient to impair passage through said membrane of said chemical.

BRIEF DESCRIPTION OF THE DRAWINGS

The above and other features and advantages of the present invention will become apparent upon reading the following detailed description of the preferred embodiments taken in conjunction with the accompanying drawings in which.

DETAILED DESCRIPTION OF THE PREFERRED EMBODIMENTS

Figure 1:
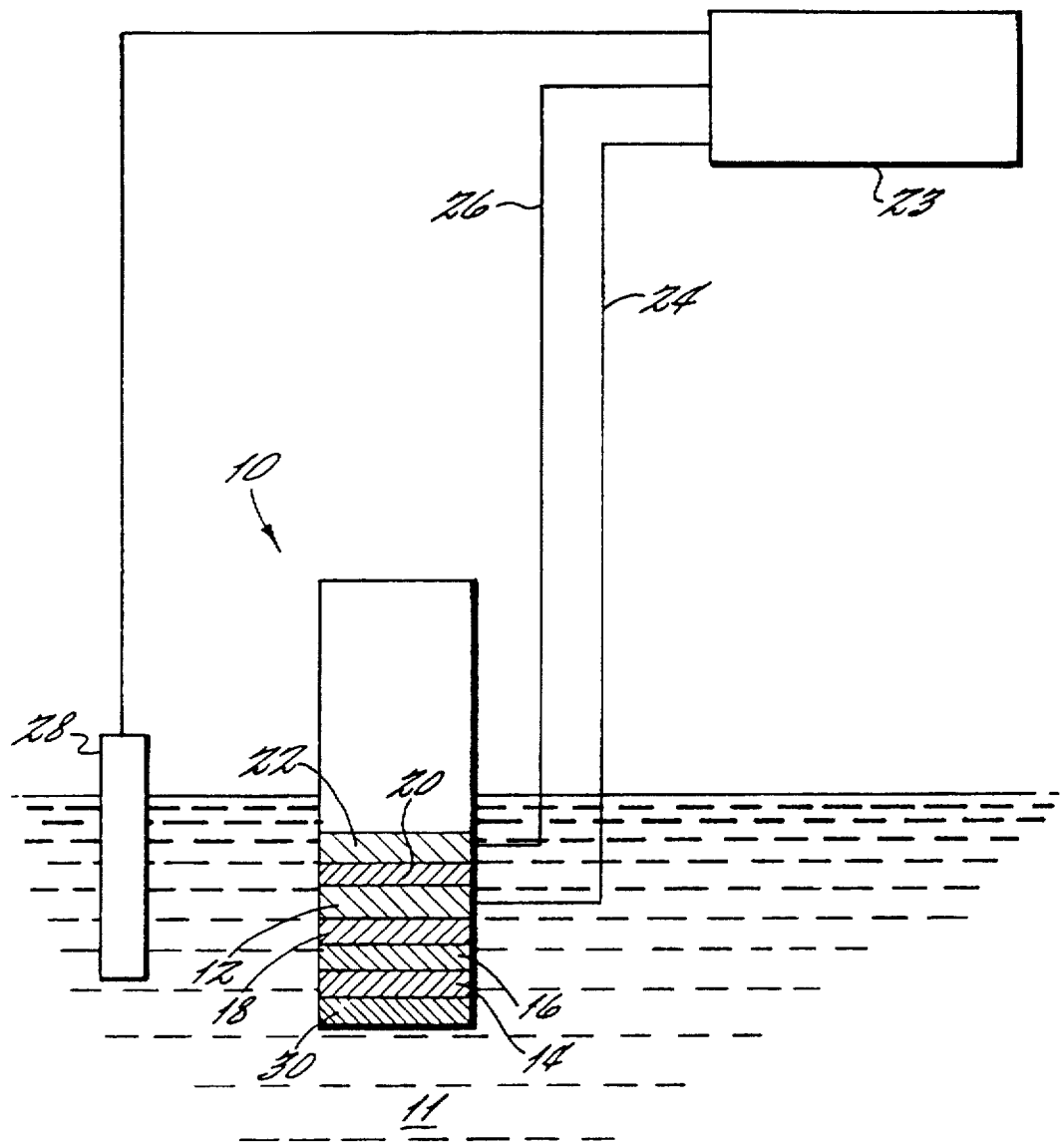
FIG. 1 is a diagrammatic drawing of a biosensor in accordance with the present invention.

Referring to the drawings for the purpose of describing preferred embodiments of the present invention, FIG. 1 is a diagrammatic view of an electrochemical biosensor 10 for determining the levels of chemicals in biological fluids. The embodiments are described with reference to an implantable glucose sensor for determining the concentration of glucose in blood sera. However, it will be appreciated that electrochemical biosensors for determining the presence of other target chemicals in fluids including oxygen, potassium, calcium, acid, base, protons, $CO_2$, sodium, chloride and the like are within the scope of the features and advantages provided by the present invention.

The biosensor 10 may take any recognized form such as disclosed in the aforementioned Gough et. al. publication and will be described with reference to the model set forth in Gough et. al., Diabetes Care, Vol. 5, No. 3, May–June 1982, pp. 190–198, which is incorporated herein by reference. Therein, the biosensor 10, immersed in a biological fluid 11, comprises an oxygen electrode 12 covered by a base membrane 14 containing an immobilized enzyme layer 16. The enzyme layer 16 comprises glucose oxidase and catalase. In the presence of glucose and oxygen, the electrode 12 produces a glucose-modulated, oxygen dependent current. It will be appreciated that this layer is not limited to an enzyme per se but in other applications may be any compound that reacts with another compound in a predictable and quantitatively measurable manner; or in other words, a specific binding pair. The enzyme layer 16 is separated from the electrode 12 by a hydrophobic, oxygen-permeable layer 18. The membrane 14 is formed of a biocompatible material such as polyurethane with a permeability that restricts access of macromolecules to the underlying layers. The layer 18 is a hydrophobic, oxygen-permeable membrane that prevents electrode fouling due to the hydrophilic electroactive molecules in biological fluids. A spacer 20 separates the electrode 12 from a counter electrode 22. The electrodes 12 and 22 are connected to an electrical system 23 by leads 24 and 26 and delivering thereto a current flux related to the electrochemical reactions within the biosensor. Additionally, the electrical system is connected to a reference electrode 28. As discussed in greater detail in the above publication, the system 23 outputs information related to the concentration of glucose in the biological fluid. The various laminae are enclosed by a housing, not shown. In the present invention, the outer surface of the base membrane 14 is covered by a biologically inert membrane 30.

As mentioned above, various materials have been proposed for biosensor membranes. Among the more prevalent membranes are polyurethane, cellulose acetate, perfluorosulfonic acid polymer and others well known in the art. Many of these materials are biocompatible in that the materials do not induce inflammation when implanted. However, these materials have well-recognized bioattractive sites that for proteins and fibrin facilitate a biological overgrowth that results in a progressive reduction in sensing area and resultant drift in electrical signal, ultimately leading to complete blockage of the membrane and loss of meaningful signal. These attractive sites typically have repeating electron donor sites including oxygen, fluorine, chlorine and the like.

In the present invention, the biologically inert membrane 30 is formed of a material characterized by a phenyl-based polymer having connecting hydrogen donors that bond to the biologically active sites, thereby presenting to the biological fluid 11 a surface comprised of non-reactive phenyl rings. A preferred membrane material is selected from the parylene family of polymers, including poly-para-xylylene, mono-chloro-para-xylylene, dichloro-para-xylylene and analogs thereof. The parylene polymers have connecting —$CH_2$— groups. Other similar based polymers have —NH— groups, —SH— groups and other limited hydrogen atom donors. These polymers bind to the active sites on the base membrane polymer through hydrogen bonding at the connecting groups. This is generally achieved with an ultra thin layer of the inert membrane material, typically 1000 Angstroms or less, and generally between 50–500 Angstroms. At this thickness, the material, vacuum deposited in the case of the parylene polymers, is applied preferentially to the active sites on the base polymer and believed substantially to the exclusion of cross linking with itself in a manner which renders the composite membrane biologically inert without affecting the desired membrane properties, such as permeability and porosity.

It does not appear necessary that the membrane 30 completely passivate all the active sites. There may be instances where a less than complete coating will provide biological protection sufficient for the membrane application. Also, the membrane may be applied in excess of the amount needed for inertness. However, the thickness should be controlled to prevent a diminution of membrane performance.

The aforementioned membrane thus provides biological passivation without a diminution of sensor sensitivity as demonstrated by the following examples.

EXAMPLE 1

A $pCO_2$ membrane (available from NOVA Biomedical, Waltham Mass. as catalog no. 07543) was coated with about 500 Angstroms of poly-para-xylylene to form a second membrane thereon. The coated membrane was tested in RPMI media on a NOVA Stat Profile 5 blood gas analyzer which combines blood gas and related stat tests of serum, plasma, whole blood and expired gas for in vitro diagnostic use. The biosensor was tested in 7 consecutive trials and indicated $pCO_2$ levels of 32.04 STD 1.15. A similar not coated membrane was tested in 6 consecutive trials and indicated $pCO_2$ levels of 28.63 STD 5.96. It is thus apparent that second membrane did not affect biosensor readability and reliability.

EXAMPLE 2

A $pO_2$ Membrane (available from NOVA Biomedical, Waltham Mass. as catalog no. 11099) was coated with about 500 Angstroms of poly-para-xylylene to form a second membrane thereon. The coated membrane was tested in RPMI media on a NOVA Stat Profile 5 blood gas analyzer which combines blood gas and related stat tests of serum, plasma, whole blood and expired gas for in vitro diagnostic use. The biosensor was tested in 7 consecutive trials and indicated $pO_2$ levels of 247.94 STD 4.44. A similar not coated membrane was tested in 6 consecutive trials and indicated $pO_2$ levels of 251.41 STD 16.39. As in the first example, it is thus apparent that second membrane did not affect biosensor readability and reliability.

EXAMPLE 3

A glucose membrane (available from NOVA Biomedical, Waltham Mass. as catalog no. 08469) was coated with less than about 500 Angstroms of poly-para-xylylene to form a second membrane thereon. The coated membrane was tested in a NOVA Stat Profile 5 blood gas analyzer which combines blood gas and related stat tests of serum, plasma, whole blood and expired gas for in vitro diagnostic use. The biosensor was tested in 8 consecutive trials and indicated glucose levels of 207.7 mg % STD 1.59. A similar uncoated membrane was tested in 10 consecutive trials and indicated glucose levels of 200.5 mg % STD 1.59. It is thus apparent that second membrane did not affect biosensor readability and reliability.

Thereafter the coated membrane and the uncoated membrane were implanted into a 4 kg New Zealand White rabbit with the membranes exposed subcutaneously. The membranes were removed after 21 hours. The uncoated membrane was occluded and overgrown with tightly adhering hematocrit which was not dislodged by repeated washings and had to be physically removed for testing. The membrane was tested in 8 trials and indicated glucose levels of 188.25 mg % STD 5.07. The coated membrane was essentially clear of any fouling and was readily washed in normal saline solution. The coated membrane was tested in 8 trials and indicated glucose levels of 207.25 mg % STD 0.7. The foregoing indicates that the uncoated membrane was adversely affected in short term implant due to biofouling whereas the membrane coated in accordance with the present invention was not subject to biofouling and did not experience any diminution in signal.

In addition to the aforementioned applications, it will be apparent to those skilled in the art that the composite membrane may be used in other biological applications wherein it is desired to protect cellular and chemical moieties from biological fouling while providing desired porosity and diffusions. Examples of such applications include indwelling chemical sensors, indwelling electrical sensors, long term drug delivery carriers that must be free from fibrin or protein occlusion to release their active ingredients or release the active agent in response to a stimulating moiety found in vivo.

While the present invention has been described with the detection of chemical and biological substances that are normally, abnormally, or pathologically present in the blood or other physiological fluids, and whose detection may be desired on a continuing basis, these chemical or biological substances may be naturally occurring within the subject in which the biosensor is implanted, or by unusual occurrence because of disease or reaction to physiological stress. Examples of such chemical and biological substances include, but are not limited to, hormones, peptides, proteins, glycoproteins, triglycerides, fats, lipids, polysaccharides, carbohydrates, vitamins, minerals, therapeutics, and metals.

As used herein, a "hormone" is defined as a biological substance secreted by a specific tissue, and includes those substances having activity at a different site than the site of secretion and precursors therof, and substances having activity at the site of secretion (sometimes called autocoids), and secreted by the pituitary gland (or adenohypophysis), and specifically include the growth hormones (GH), melanocyte-stimulating hormones, somatomedins, and lipotropins.

The biosensor of the present invention may also be useful in the detection of compounds that are normally found within the brain and which secrete neurologically active substances. Therefore, the detection of neuropeptides may be provided in the practice of the invention, including the detection of neuropeptide families of the endorphins, the glucagon-secretins, and the substance-P neuropeptides. Endorphins include the proopiomelanocortins, the proenkephalins, the prodynorphins and hormones derived therefrom. The glucagon-secretins include glucagon, vasoactive intestinal polypeptide (both found in pancreatic islets), secretin and growth hormone releasing factor (GHRF). The substance-P neuropeptides include vasotocin, vasopressin and oxytocin. It is specifically intended that the detection of substances secreted by single large clusters of neurons (such as oxytocin, vasopressin, LHRH, GHRH, and proopiomelanocortin) are embraced by the scope of the invention, as well as the detection of substances secreted by cells normally distributed throughout the brain (such as somatostatin, cholecystokinin and enkephalin).

The continuing detection of vitamins present in blood and other fluids is another aspect of the invention. This aspect is particularly useful in monitoring vitamin levels in subjects who are at risk for vitamin deficiencies. Such vitamins include vitamin A, thiamine, riboflavin, nicotinic acid, vitamin $B_6$, vitamin D, iron, folic acid, and vitamin $B_{12}$. The detection of vitamins via their reactions with specific enzymes is known. For example, the presence of thiamine can be detected by its reaction with the enzymes erythrocyte transketolase (ETK) and thiamine pyrophosphate (TPP). Similarly, the presence of riboflavin may be detected by its known reaction with erythrocyte glutathione reductase (EGR). Vitamin $B_6$ may be detected by its reaction with erythrocyte glutamic-oxaloacetic transaminase (EGOT), and vitamin D may be detected by its reaction with serum alkaline phosphatase.

Antibodies which may be detected by the biosensor of the present invention include those of the immunoglobulin family, including IgA, IgD, IgE, IgG and IgM. The detection of other immunological compounds and cells are a further aspect of this invention. These other immunological compounds and cells include interleukins, cytokines, major histocompatibility complexes (MHC), T cells, complement, and macrophages.

The presence of drugs, other therapeutics and their metabolites may be detected by the biosensor of the present invention by known individual reactions with drug-specific enzymes and other reactive compounds. By drugs is meant any pharmaceutical with an intended and known therapeutic or diagnostic value, but may also mean an illegal or controlled substance whose detection is desired for forensic or monitoring reasons.

The present invention is concerned primarily with the treatment of human subjects, but may also be employed for the treatment of other mammalian subjects, such as cows, pigs, goats, cats, and dogs, for veterinary purposes, or where compounds detected by the biosensor are being produced in the animal for subsequent collection and the like.

One embodiment of the invention is the use of an electrobiochemical biosensor to detect substances such as hormones, glucose, drugs, and the like in animals, for veterinary and/or agricultural purposes. As an example, growth hormones are sometimes administered to an animal subject for the purpose of increasing meat production. However, at excessively high concentrations, such a hormone may cause deleterious effects in the consumer. A biosensor provided by the present invention which comprises a substrate reactive with such a hormone may therefore be implanted in such a meat-producing animal to provide a means of monitoring such levels on an ongoing basis.

Various modifications of the above described embodiments will be apparent to those skilled in the art. Accordingly, the scope of the invention is defined only by the accompanying claims.

What is claimed:

1. An electrochemical biosensor for determining in vivo in a mammal the level of a target chemical in a biological fluid, said biosensor comprising:

an electrochemical system including a substrate which reacts with the target chemical to yield a system signal related to the concentration in the biological fluid of said target chemical;

a first membrane immobilizing said substrate and having a porosity permitting passage therethrough of the target chemical to react with said substrate, said first membrane having a surface characterized by electron donor sites susceptible to facilitating attachment thereon of proteins and fibrin, thus impairing said system signal; and a second membrane bonded to said electron donor sites of and surrounding said first membrane, said second membrane being formed of poly-para-xylylene having connecting hydrogen atom donors, said hydrogen atom donors bonding to said electron donor sites of said first membrane at least sufficiently to form an outer surface on said first membrane without significantly changing the porosity provided by said first membrane, wherein said outer surface is exposed to the biological fluid and consists of phenyl rings;

and wherein said biosensor is implanted in a mammalian subject without biological fouling.

2. An electrochemical biosensor according to claim 1, wherein said second membrane has a thickness of less than about 1000 Angstroms.

3. An electrochemical biosensor according to claim 1, wherein said second membrane has a thickness of between about 50 and about 500 Angstroms.

4. An electrochemical biosensor according to claim 1, wherein said target chemical is glucose.

5. An electrochemical biosensor according to claim 1, wherein said substrate comprises glucose oxidase.

6. A biologically inert membrane composite substrate implanted in a mammal, comprising:

a first membrane characterized by a porosity permitting passage therethrough of a target chemical and formed of a material having biologically active surface sites that support protein and tissue attachment when exposed to biological fluids; and a second membrane consisting of poly-para-xylylene having connecting hydrogen donors bonded to said biologically active surface sites sufficiently to render said sites biologically inert without significantly affecting said porosity of said first membrane wherein only the phenyl rings of the second membrane are exposed, and wherein said membrane composite substrate is implanted within a mammalian subject without biological fouling.

7. A biologically inert membrane composite substrate according to claim 6, wherein said second membrane has a thickness of less than about 1000 Angstroms.

8. A biologically inert membrane composite substrate according to claim 6, wherein said second membrane has a thickness of between about 50 and about 500 Angstroms.

9. A method for biologically passivating a membrane having a porosity permitting passage therethrough of a chemical in a biological fluid and a surface with attractive sites for proteins and fibrin, comprising applying to said membrane a coating of poly-para-xylylene having connecting hydrogen bond donors bonded to said attractive sites in an amount sufficient to render said surface biologically inert but insufficient to impair passage through said membrane of said chemical.

10. A method according to claim 9, wherein said poly-para-xylylene coating is applied to said membrane by vacuum deposition.

11. A cellular or chemical moiety which has been coated with a membrane, said membrane comprising poly-para-xylylene, wherein said moiety is implanted within a mammalian subject without biological fouling.

* * * * *

UNITED STATES PATENT AND TRADEMARK OFFICE
CERTIFICATE OF CORRECTION

PATENT NO. : 5,776,324
DATED : July 7, 1998
INVENTOR(S) : Usala

It is certified that error appears in the above-identified patent and that said Letters Patent is hereby corrected as shown below:

On the title page, under item [56] References Cited and Other Publications:

Column 1, line 31, delete "et al.".
Column 1, line 42, "HAhn" should read --Hahn--.
Column 1, line 44, delete "1984".
Column 1, line 45, "registry" should read --Registry--.
Column 2, line 3, delete "1993".
Column 2, line 7, "unknow 1990." should read --unknown--.
Column 2, line 8, "A" should read --A2--; "MFG Co," should read --Mfg. Co.,--.
Column 2, line 9, "1985/" should read --1985.--.
Column 2, line 11, "Glucos" should read --Glucose--.
Column 2, line 13, "Diabets" should read --Diabetes--.
Column 2, line 14, "5" should read --5.--.

Signed and Sealed this

Sixteenth Day of February, 1999

Attest:

Attesting Officer

*Acting Commissioner of Patents and Trademarks*